(12) United States Patent
Boeke (10) Patent No.: US 7,544,470 B2
(45) Date of Patent: Jun. 9, 2009

(54) METHOD FOR FINDING MUTATIONS CAUSED BY THE INSERTION OF REPEATED DNAS

(75) Inventor: Jef D. Boeke, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/558,803

(22) PCT Filed: May 18, 2004

(86) PCT No.: PCT/US2004/015740

§ 371 (c)(1),
(2), (4) Date: Nov. 1, 2006

(87) PCT Pub. No.: WO2004/106490

PCT Pub. Date: Dec. 9, 2004

(65) Prior Publication Data

US 2007/0099188 A1    May 3, 2007

Related U.S. Application Data

(60) Provisional application No. 60/473,657, filed on May 28, 2003.

(51) Int. Cl.
C12Q 1/68        (2006.01)
C12P 19/34       (2006.01)
C07H 21/04       (2006.01)

(52) U.S. Cl. .................. 435/6; 435/91.2; 536/24.31; 536/24.32; 536/24.33

(58) Field of Classification Search .............. 435/6, 435/91.2; 536/24.33, 24.31, 24.32
See application file for complete search history.

(56) References Cited

U.S. PATENT DOCUMENTS

| 5,741,677 | A | * | 4/1998 | Kozlowski et al. ......... 435/91.2 |
| 6,083,701 | A | * | 7/2000 | Reeve .............................. 435/6 |
| 6,322,978 | B1 | | 11/2001 | Kahn et al. |
| 2004/0248144 | A1 | * | 12/2004 | Mir ................................ 435/6 |

* cited by examiner

*Primary Examiner*—Suryaprabha Chunduru
(74) *Attorney, Agent, or Firm*—Edwards Angell Palmer & Dodge LLP; Peter F. Corless; Jonathan M. Sparks (57) ABSTRACT

The present invention provides a method for identifying repeat insertion mutation, a method for identifying or classifying genetic diseases characterized by genome rearrangement, as well as a method for mapping complex traits controlled by repeat insertion mutations in a plant or mammalian subject.

19 Claims, 7 Drawing Sheets

METHOD FOR FINDING MUTATIONS CAUSED BY THE INSERTION OF REPEATED DNAS

This application claims the benefit of U.S. Provisional Application No. 60/473,657, filed on May 28, 2003, which is incorporated herein by reference in its entirety.

FIELD OF THE INVENTION

This invention relates to methods of identifying genetic mutations, especially, to identifying repeat insertion mutations.

BACKGROUND OF THE INVENTION

Retrotransposons are very abundant mobile components of the human genome and move from one site to another within the genome via an RNA intermediate and reverse transcription and often insert within genes. Retrotransposons are thus distinct from DNA transposons, which move directly at the level of DNA. In the human genome, retrotransposons outnumber DNA transposons. DNA transposons, however, also insert into genes.

The L1 element (also known as a LINE) has been extremely successful at colonizing the human genome. Early approximations estimated that L1s are present at 100,000 copies in the human genome and comprise 5% of nuclear DNA (Fanning and Singer, 1987, Biochim Biophys Acta 910: 203-121). However, recent studies suggest that as many as 520,000 L1s may exist in the human genome and comprise 17% of the human genome. (Smit, 1999, Current Opinion in Genetics and Development).

Some human L1 elements can retrotranspose (express, cleave their target site, and reverse transcribe their own RNA using the cleaved target site as a primer) into new sites in the human genome, leading to genetic disorders. Germ line L1 insertions into the factor VIII and dystrophin gene give rise to hemophilia A and muscular dystrophy, respectively (Kazazian et al., 1988, Nature 332:164-166; Narita et al., 1993, J. Clinical Invest. 91:1862-1867; Holmes et al., 1994, Nature Genetics 7:143-148), while somatic cell L1 insertions into the c-myc and APC tumor suppressor gene are implicated in rare cases of breast and colon cancer, respectively (Morse et al., Nature 333:87-90; Miki et al., 1992, Cancer Research 52:643-645). Thus, L1 is a potential mutagen and L1 retrotransposition is mutagenic.

There is a profound ascertainment bias in genetic mutation analysis in general because longer PCR products may amplify less well than shorter ones. In addition, not all mutations that cause disease are mutations in coding regions. The vast majority of known mutations are present in coding regions (including a small number of mutations that are not strictly speaking in the coding regions such as splice junction mutations which are nevertheless easily discovered because they lie so close to exons). It is very difficult and costly to find the mutations that do not fall in coding regions. There is a need in the art for a more cost effective method to identify genetic mutations.

SUMMARY OF THE INVENTION

The present invention provides a method for identifying a repeat insertion mutation, a method for identifying or classifying genetic diseases, and method for mapping complex traits controlled by repeat insertion mutations in a plant or mammalian subject characterized by genome rearrangement.

We have now found that repeat insertion mutations may be easily found and classified by using repeat array analysis and that complex traits and diseases caused by complex traits can be mapped. We have also found that this invention is useful for diagnosis of complex disease traits.

In certain aspects, a method for identifying a repeat insertion mutation is disclosed. In certain embodiments, the method comprises hybridizing copies of one or more DNA segments from mammalian subjects affected and unaffected by the mutation to a Human Repeat Array, and determining the ratio of segments containing human repeat sequences present in affected subject samples relative to human repeat sequences present in unaffected subject samples. In certain preferred embodiments the repeat insertion mutation is an L1 insertion mutation.

In certain other embodiments the Human Repeat Array contains all known human repeat sequences.

In another aspect a method for identifying or classifying genetic diseases characterized by genome rearrangement is disclosed. The method comprises hybridizing copies of one or more DNA segments from mammalian subjects affected and unaffected by the genetic disease to a Human Repeat Array, and determining the ratio of segments containing human repeat sequences present in affected subject samples relative to human repeat sequences present in unaffected subject samples.

In yet another aspect, a method for mapping complex traits controlled by repeat insertion mutations in a plant or mammalian subject comprises hybridizing copies of one or more DNA segments from such subject exhibiting and not exhibiting the trait to a Human Repeat Array, and determining the ratio of segments containing human repeat sequences present in trait-exhibiting subject samples relative to human repeat sequences present in non-trait-exhibiting subject samples.

Another aspect provided herein is a kit for identifying a repeat insertion mutation, the kit comprising a Human Repeat Array.

DESCRIPTION OF THE DRAWINGS

FIG. 2A shows the transcription unit from FIG. 1, which is analyzed using primer pairs spanning the entire transcription unit. FIG. 2B shows a comparison between amplicons from affected and unaffected individuals, which will reveal a length polymorphism present in the affected individual if the affected individual has a repeat insertion (red bar). Only a portion of the transcription unit is shown for clarity. FIG. 3C shows electrophoretic separation of the amplicons and reveals the length polymorphism in both affected heterozygotes or homozygotes. The affected amplicon length is larger than the wild-type amplicon length by the length of the insertion.

FIG. 3A shows the transcription unit from FIG. 1, which is analyzed using primers spanning the entire transcription unit in combination with one or more repeat-specific primers. The gene specific primers may need to be labeled because the repeat specific primers may generate a complex pattern of bands obscuring the desired result. FIG. 3B shows that a comparison between amplicons from affected and unaffected individuals will reveal a length polymorphism present in the affected individual if the affected individual has a repeat insertion (red bar). Only a portion of the transcription unit is shown for clarity. FIG. 3C shows electrophoretic separation of the amplicons, which reveals a length polymorphism in both affected heterozygotes or homozygotes as shown. The mutation specific band may be either larger (as shown) or shorter than the wild-type amplicon length.

FIG. 4A demonstrates that the transcription unit from FIG. 1 is analyzed using primer pairs spanning the entire transcription unit. FIG. 4B shows that a comparison between amplicons from affected and unaffected individuals will reveal a length polymorphism present in the affected individual if the affected individual has a repeat insertion (red bar). Only a portion of the transcription unit is shown for clarity. FIG. 4C shows pooled amplicons with a pool size P to be empirically determined, which is mixed with control gene amplicons that are represented on the HuRA. Amplicon pools from affected subjects are individually hybridized to HuRAs, as are amplicon pools from either pooled or individual unaffected control DNAs. Amplicon pools with an elevated repeat hybridization ratio "R" are identified. Pools are resolved to identify the amplicon carrying the mutation using the same technique, and the relevant gene region is sequenced.

FIG. 5 shows a portion of the Human Repeat Array. The array could be any two dimensional or three dimensional surface containing bound oligonucleotides of a defined sequence well-known in the art. A small segment of one repeat element (here the human L1 sequence is used as an example) is represented on the array by a tiled set of oligonucleotides of length o. Note that this design allows the repeat endpoints to be mapped, which is useful because many human repeats are truncated and their expression-inhibiting power depends on their length. Thus longer repeat insertions are more likely to result in inhibition of expression of the target gene. Oligonucleotides could be nonoverlapping as shown or overlapping to increase statistical power and endpoint mapping precision.

DETAILED DESCRIPTION OF THE INVENTION

Disclosed herein is a method for identifying a genetic mutation, especially repeat insertion mutations. Repeat insertion mutations include mutations caused by transposons, retrotransposons, repeat expansions, chromosomal rearrangement, and chromosomal translocations. Included are repeat sequences known to be transposable and repeat sequences not known to be transposable. For example, a repeat insertion mutation may be an L1 insertion mutation, a trinucleotide repeat expansion mutation, a transposon mutation, and a retrotransposon mutation. One of skill in the art would know how to recognize other mutations that could be identified using this invention. Insertion mutations are 20-fold more likely to fall in non-coding regions than into coding regions because noncoding regions are actually for insertion because of their higher A/T content. Insertion mutations often go undetected because they often reduce but do not necessarily eliminate gene expression. Thus the methods taught herein are useful for identifying genetic mutations characterized by variability at the level of expressivity, penetrance, and phenotypic manifestation.

Insertional mutations includes the translocation of nucleic acid from one location to another location which is in the genome of an animal so that it is integrated into the genome, thereby creating a mutation in the genome. Insertional mutation also includes repeat expansion.

A "retrotransposition event" is used herein to refer to the translocation of a retrotransposon from a first location to a second location with the preferable outcome being integration of a retrotransposon into the genome at the second location.

There are many known methods of amplifying nucleic acid sequences including e.g., PCR See, e.g., PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. Nos. 4,683,202, 4,683,195, 4,800,159, 4,965,188 and 5,333,675 each of which is incorporated herein by reference in their entireties for all purposes.

The DNA polymerase used in PCR is often a thermostable polymerase. This allows the enzyme to continue functioning after repeated cycles of heating necessary to denature the double stranded DNA. Polymerases that are useful for PCR include, for example, Taq DNA polymerase, Tth DNA polymerase, Tfl DNA polymerase, Tma DNA polymerase, Tli DNA polymerase, Pfx DNA polymerase and Pfu DNA polymerase. There are many commercially available modified forms of these enzymes including: AmpliTaq.RTM. AmpliTaq.RTM. Stoffel Fragment and AmpliTaq Gold.RTM. available from Applied Biosystems (Foster City, Calif.). Many are available with or without a 3- to 5' proofreading exonuclease activity. See, for example, Vent.RTM. and Vent.RTM. (exo-) available from New England Biolabs (Beverly, Mass.).

Other suitable amplification methods include the ligase chain reaction (LCR) (e.g., Wu and Wallace, Genomics 4, 560 (1989) and Landegren et al., Science 241, 1077 (1988)), transcription amplification (Kwoh et al., Proc. Natl. Acad. Sci. USA 86, 1173 (1989)), self-sustained sequence replication (Guatelli et al., Proc. Nat. Acad. Sci. USA, 87, 1874 (1990)) and nucleic acid based sequence amplification (NABSA). (See, U.S. Pat. Nos. 5,409,818, 5,554,517, and 6,063,603 each of which is incorporated herein by reference in their entireties).

A subject is not limited to a human being but may also be other organisms including but not limited to mammals, plants, bacteria, or cells derived from any of the above.

As used herein, affected includes, subjects that have or may have an insertional mutation and unaffected refers to a subject not suffering from an insertional mutation. The unaffected DNA can be a wild type fraction similar to the affected DNA. This unaffected DNA likely will have no, mutations. The control nucleic acid can be selected depending upon the intent of the test. For example, where acquired mutations in cancer cells are being screened, the control nucleic acid can come from a "normal" cell from the same individual. In other instances, for example, where an inherited (genetic) component may be involved, the control DNA would come from a different subject than the individual the nucleic acid; or simply differences among the paternal and maternal alleles can be examined by a self-hybridization of the DNA of the examined individual. Methods of the invention include global DNA sequencing. Mapping of insertional mutations may be done by obtaining the entire genome sequences of affected and unaffected individuals, assembling all repeat regions properly and compare the repeat regions.

Repeat arrays are arrays of oligonucleotides. The arrays may contain one or more genomic repeated sequence from the genome of, for example, a bacteria, a yeast, a mammal. One of skill in the art, having the benefit of this disclosure, would know how to identify relevant repeat sequences to include in the array.

The Human Repeat Array (HuRa) is an array of oligonucleotides. The array may have one or more human repeat. For example, the array may have the L1 repeat arrayed on the surface, or the array may contain the L1 family. IN certain preferred embodiments, the Human Repeat Array contains all known human repeat sequences. In other preferred embodiments, the Human Repeat array contains oligonucleotide probes of a length spanning all known human repeat sequences. In other embodiments, the Human Repeat Array includes both repeat sequences known to be transposable and repeat sequences not known to be transposable. In still other embodiments, the repeat sequences not known to be transposable include rDNAs, tRNAs, satellite DNAs, and expandable DNAs.

The ratio of segments containing human repeat sequences present in affected subject samples relative to human repeat sequences present in unaffected subject samples.

A method for identifying or classifying genetic diseases characterized by genome rearrangement, includes the identification or classification of types of tumors, types of neurological disorders, types of dermatological disorders, types of muscular disorders, and the like. Complex traits may also be mapped, identified or classified. The complex traits may be from mammals or plants.

This invention also provides kits for identifying a repeat insertion mutations. The kit may provide a Human Repeat Array. The kit may also include reagents for long PCR The kit may alternately provide unaffected sample nucleic acid.

In certain embodiments, the DNA copies are generated by long polymerase chain reaction using primers. One skilled in the art will be able to generate primers suitable for amplifying target sequences of additional nucleic acids, such as those flanking loci of known repeat insertion mutation sequences, using routine skills known in the art and the teachings of this invention. In certain embodiments the primer pairs are spaced about 1000 nucleotides or less apart. In others, the primer pairs are spaced more than about 1000 nucleotides apart. The primer pairs may directly flank pre-existing repeat sequences. The primer pairs may also be spaced throughout flanking regions upstream and downstream of the transcription unit of interest.

In general, the primers used according to the method of the invention embrace oligonucleotides of sufficient length and appropriate sequence which provide specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15-22 or more nucleotides, although it may contain fewer nucleotides as long as the primer is of sufficient specificity to allow essentially only the amplification of the specifically desired target nucleotide sequence (i.e., the primer is substantially complementary). The exact length of primer will depend on many factors, including temperature, buffer, and nucleotide composition. Substantially complementary means that the primers must be sufficiently complementary to hybridize with their respective strands under conditions which allow the agent for polymerization to function. In other words, the primers should have sufficient complementarily with the flanking sequences to hybridize with and permit amplification of the nucleotide sequence. Preferably, the 3' terminus of the primer that is extended has perfectly base paired complementarity with the complementary flanking strand. The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

As used herein, "gene" includes "transcription unit" and "intergene" includes the sequences between transcription units.

The nucleic acid from any subject, in purified or nonpurified form, can be utilized as the starting nucleic acid for an amplification reaction. Thus, the process may employ, for example, DNA or RNA, including messenger RNA (mRNA), wherein DNA or RNA may be single stranded or double stranded. In the event that RNA is to be used as a template, enzymes, and/or conditions optimal for reverse transcribing the template to DNA would be utilized. A mixture of nucleic acids may also be employed, or the nucleic acids produced in a previous amplification reaction herein, using the same or different primers may be so utilized. The mutant nucleotide sequence to be amplified may be a fraction of a larger molecule or can be present initially as a discrete molecule, such that the specific sequence constitutes the entire nucleic acid. It is not necessary that the sequence to be amplified be present initially in a pure form; it may be a minor fraction of a complex mixture, such as contained in whole human DNA.

Hybridizing copies of DNA segments, as used herein includes the ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. Hybridization: two nucleic acid molecules may be hybridized, although the base pairing is not completely complementary. Accordingly, mismatched bases do not prevent hybridization of two nucleic acid molecules provided that appropriate conditions, well known in the art, are used.

Other terms used in the fields of recombinant DNA technology and molecular and cell biology as used herein will be generally understood by one of ordinary skill in the applicable arts.

The product of the amplification reaction may be the oligonucleotide probe. I don't understand the previous sentence. The oligonucleotide probe may be least about 16 nucleotides in length. In certain embodiments, the oligonucleotide probe may be less than about 200 nucleotides in length. Alternately, the oligonucleotide probe may be less than about 100 nucleotides in length.

The invention contemplates analyzing one or more DNA segments of interest. The method is not limited to a single DNA segment of interest.

The term "probe" refers to a single-stranded nucleic acid molecule that can base pair with a complementary single stranded target nucleic acid to form a double-stranded molecule.

The term "label" will refer to a substance which may be incorporated into DNA or RNA which will emit a detectable signal under various conditions. Typically a label will be a fluorescent moiety.

"Coding sequence" or "open reading frame" (ORF) refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences. "Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression," as used herein, refers to the transcription and stable accumulation of sense (mRNA) or antisense RNA derived from genomic DNA. Expression may also refer to translation of mRNA into a polypeptide.

Signal generating labels that may be incorporated into the probes are well known in the art. For example labels may include but are not limited to fluorescent moieties, chemiluminescent moieties, particles, enzymes, radioactive tags, or light emitting moieties or molecules, where fluorescent moieties are preferred. Most preferred are fluorescent dyes capable of attaching to nucleic acids and emitting a fluorescent signal. A variety of dyes are known in the art such as fluorescein, Texas red, and rhodamine. Preferred in the present invention are the mono reactive dyes cy3 (146368-16-3) and cy5 (146368-14-1) both available commercially (i.e. Amersham Pharmacia Biotech, Arlington Heights, Ill.). Suitable dyes are discussed in U.S. Pat. No. 5,814,454 hereby incorporated by reference. Labels may be incorporated by any of a number of means well known to those of skill in the art. However, in a preferred embodiment, the label is simultaneously incorporated during the amplification step in the preparation of the probe nucleic acids. Thus, for example, polymerase chain reaction (PCR) with labeled primers or labeled nucleotides will provide a labeled amplification roduct. In a preferred embodiment, reverse transcription or replication, using a labeled nucleotide (e.g. dye-labeled UTP and/or CTP) incorporates a label into the transcribed nucleic acids. Alternatively, a label may be added directly to the original nucleic acid sample (e.g., mRNA, polyA mRNA, cDNA, etc.) or to the amplification product after the synthesis is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore). Following incorporation of the label into the probe the probes are then hybridized to the micro-array using standard conditions where hybridization results in a double stranded nucleic acid, generating a detectable signal from the label at the site of capture reagent attachment to the surface. Typically the probe and array must be mixed with each other under conditions which will permit nucleic acid hybridization. This involves contacting the probe and array in the presence of an inorganic or organic salt under the proper concentration and temperature conditions. The probe and array nucleic acids must be in contact for a long enough time that any possible hybridization between the probe and sample nucleic acid may occur. The concentration of probe or array in the mixture will determine the time necessary for hybridization to occur. The higher the probe or array concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) Nucl. Acids Res. 19:5143-5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30-50% (v/v). Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate. Methods of optimizing hybridization conditions are well known to those of skill in the art (see, e.g., Laboratory Techniques in Biochemistry and Molecular Biology, Vol. 24: Hybridization With Nucleic Acid Probes, P. Tijssen, ed. Elsevier, N.Y., (1993)) and Maniatis, supra.

Stringent hybridization conditions are considered to be hybridization in a buffered solution of 0.9 M NaCl at 55.degree. Comparable hybridization stringency can be established at other salt concentrations and temperatures. This is accomplished, for example, by the inclusion of organic denaturants such as formamide in the hybridization buffer. Standard molecular hybridization techniques include, in situ hybridization, Southern blotting, and colony hybridization, employing the sequence (See, e.g., Ausubel et al., Current Protocols in Molecular Biology, John Wiley & Sons (1998); and Sambrook et al., Molecular Cloning: A Laboratory Manual, 2nd Ed. (1989)).

Isolated DNA, as used herein, refers to a DNA sequence which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid (e.g., RNA, DNA or protein) in its natural state.

Complementary refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

Copies of one or more DNA segments may be generated by methods well known in the art, including but not limited to, PCR, RT-PCR, and the like.

A first region of an oligonucleotide is "flanking" a second region of an oligonucleotide if the two regions are adjacent one another or if the two regions are separated by no more than about 1000 nucleotide residues, and preferably no more than about 100 nucleotide residues.

A first region of an oligonucleotide is "flanking" a second region of an oligonucleotide if the two regions are adjacent one another or if the two regions are separated by no more than about 1000 nucleotide residues, and preferably no more than about 100 nucleotide residues.

As used in this application, the singular form "a," "an," and "the" include plural references unless the context clearly dictates otherwise. For example, the term "an agent" includes a plurality of agents, including mixtures thereof.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, N.Y., Gait, "Oligonucleotide Synthesis: A Practical Approach" 1984, IRL Press, London, Nelson and Cox (2000), Lehninger, Principles of Biochemistry 3.sup.rd Ed., W. H. Freeman Pub., New York, N.Y. and Berg et al. (2002) Biochemistry, 5.sup.th Ed., W. H. Freeman Pub., New York, N.Y., all of which are herein incorporated in their entirety by reference for all purposes.

The present invention can employ solid substrates, including arrays in some preferred embodiments. Repeat arrays containing repeat sequences from genomes are contemplated. For example, repeat sequences from bacteria, yeast, frogs, and mammals are contemplated. Human Repeat Arrays (HuRa arrays) are especially contemplated. A HuRA may represent all known human repeats, or one or more of the repeats. Examples of repeats include, L1-like repeats, SINEs, LTR-retrotransposons, endogenous retroviruses, DNA transposons and related sequences, rDNA, tRNAs, and satellite DNAs, including tri-nucleotide repeat expansions.

Methods and techniques applicable to polymer (including protein) array synthesis have been described in U.S. Ser. No. 09/536,841, WO 00/58516, U.S. Pat. Nos. 5,143,854, 5,242, 974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes. Patents that describe synthesis techniques in specific embodiments include U.S. Pat. Nos. 5,412,087, 6,147,205, 6,262, 216, 6,310,189, 5,889,165, and 5,959,098. Nucleic acid arrays that are useful in the present invention include those that are commercially available from Affymetrix (Santa Clara, Calif.)

The present invention also contemplates sample preparation methods in certain preferred embodiments. Prior to or concurrent with mutation detection, the genomic sample may be amplified by a variety of mechanisms, some of which may employ PCR. See, e.g., PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference. Other suitable amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guateri et al., Proc. Nat. Acad. Sci. USA, 87, 1874 (1990) and WO90/ 06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242, 794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2.sup.nd Ed. Cold Spring Harbor, N.Y, 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between DNA segments in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; 6,225,625, and 6,344,316 in U.S. Patent application No. 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application No. 60/364,731 and in PCT Application PCT/US99/06097 (published as WO99/47964), each of which also is hereby incorporated by reference in its entirety for all purposes. The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2.sup-nd.nd., 2001). The present invention may also make use of various computer program products and software for a variety of purposes, such as probe design, management of data, analysis, and instrument operation. See, U.S. Pat. Nos. 5,593, 839, 5,795,716, 5,733,729, 5,974,164, 6,066,454, 6,090,555, 6,185,561, 6,188,783, 6,223,127, 6,229,911 and 6,308,170.

Nucleic acids according to the present invention may include any polymer or oligomer of pyrimidine and purine bases, preferably cytosine (C), thymine (T), and uracil (U), and adenine (A) and guanine (G), respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The analogs are those molecules having some structural features in common with a naturally occurring nucleoside or nucleotide such that when incorporated in a nucleic acid or oligonucleotide sequence, they allow hybridization with a naturally occurring nucleic acid sequence. An oligonucleotide or polynucleotide is a single-stranded nucleic acid ranging from at least 2, preferably at least 8, 15 or 20 nucleotides in length, but may be up to 50, 100, 1000, or 5000 nucleotides long or a compound that specifically hybridizs to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. "Polynucleotide", "nucleic acid" and "oligonucleotide" are used interchangeably in this application. The term fragment, segment, or DNA segment refers to a portion of a larger DNA polynucleotide or DNA. A polynucleotide, for example, can be broken up, or fragmented into, a plurality of segments. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

A number of methods disclosed herein require the use of restriction enzymes to fragment the nucleic acid sample.

"Genome" designates or denotes the complete, single-copy set of genetic instructions for an organism as coded into the DNA of the organism. A genome may be multi-chromosomal such that the DNA is cellularly distributed among a plurality of individual chromosomes. For example, in human there are 22 pairs of chromosomes plus a gender associated XX or XY pair.

An allele refers to one specific form of a gene within a cell or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations".

At each autosomal specific chromosomal location or "locus" an individual possesses two alleles, one inherited from the father and one from the mother. An individual is "heterozygous" at a locus if it has two different alleles at that locus. An individual is "homozygous" at a locus if it has two identical alleles at that locus.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

EXAMPLES

All documents mentioned herein are incorporated herein by reference in their entirety. The following non-limiting examples are illustrative of the invention.

Example 1

Search for Length Polymorphisms.

Figure 1:
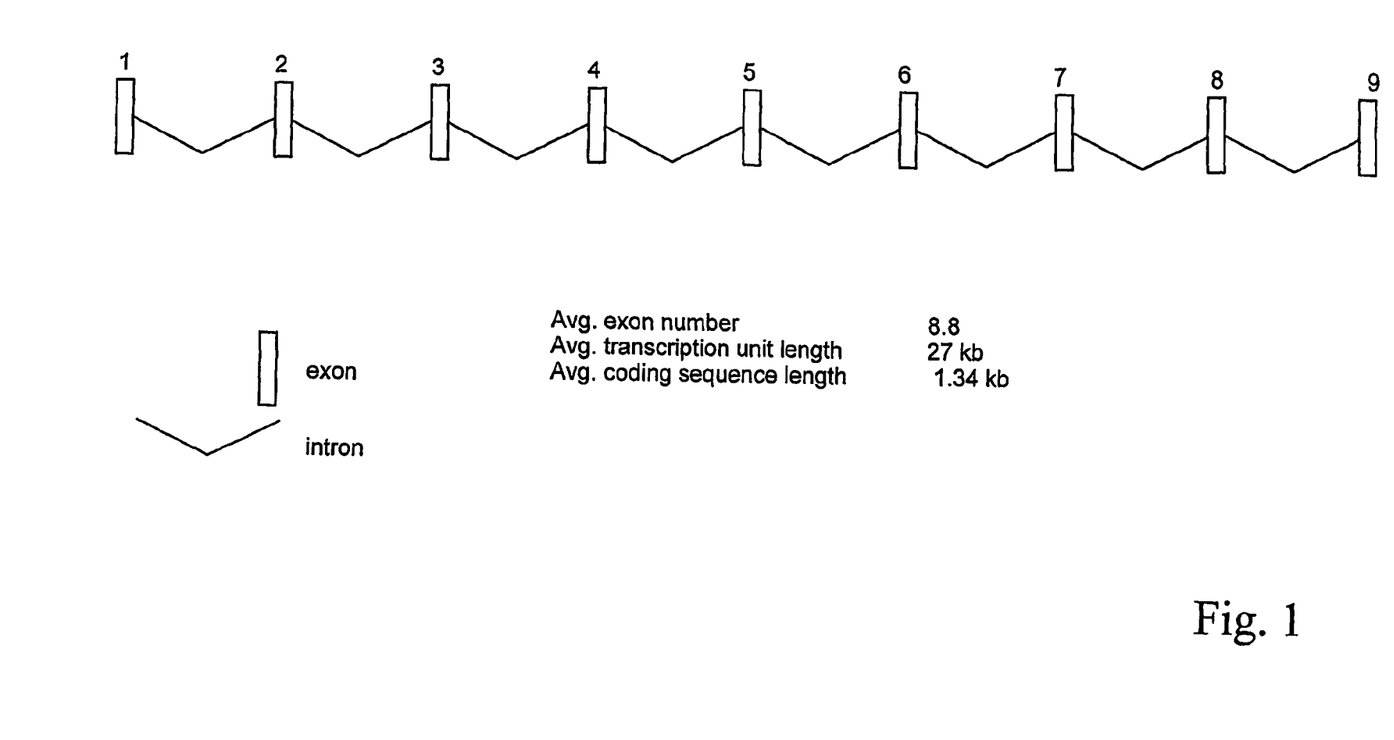
FIG. 1 shows the characteristics of an average human transcription unit and is based on Lander et al. (2001).
Figure 2:
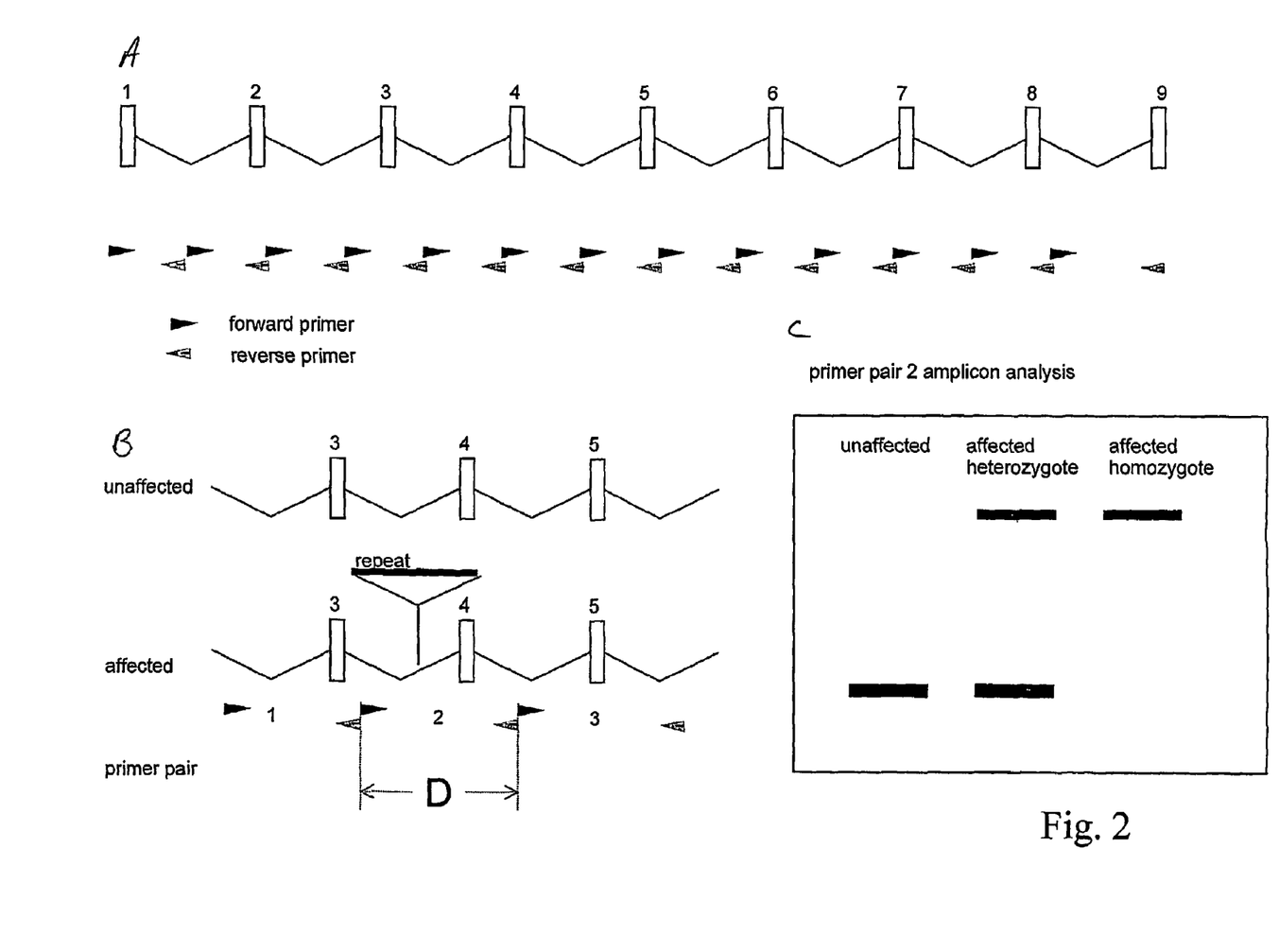
FIG. 2 demonstrates a method for identifying repeat insertions based on comprehensive amplicon length analysis using electrophoretic separation.

This method is outlined in FIG. 2. PCR (polymerase chain reaction) or related DNA amplification methods are employed to amplify insertion alleles up to 6 kb (the length of an L1 element) longer than the distance "D" between primer pairs (specifying the wild-type amplicon length). The primer pairs could be spaced every 1000 nucleotides (e.g.) throughout the transcription unit of interest and long PCR or related methods used to amplify the segments. The amplicons are electrophoretically separated to determine their size and the patterns are examined for the presence of bands larger than the predicted wild-type amplicon length. This method makes no assumption about the type of DNA inserted and thus it could detect new insertions from active transposon families as well as ancient insertions from transposon families that would be difficult to detect by other methods. If the insertion allele is heterozygous the intensity of the larger band will be weaker than that of the normal band and thus may escape detection. The amplification reactions may product spurious products of unpredictable sizes that might be unrelated to the desired insertion allele product. The heterozygous bands and the spurious products would have to be followed up to determine whether or not they were real insertion allele products.

Example 2

Search for Repeat-Specific Amplicons.

Figure 3:
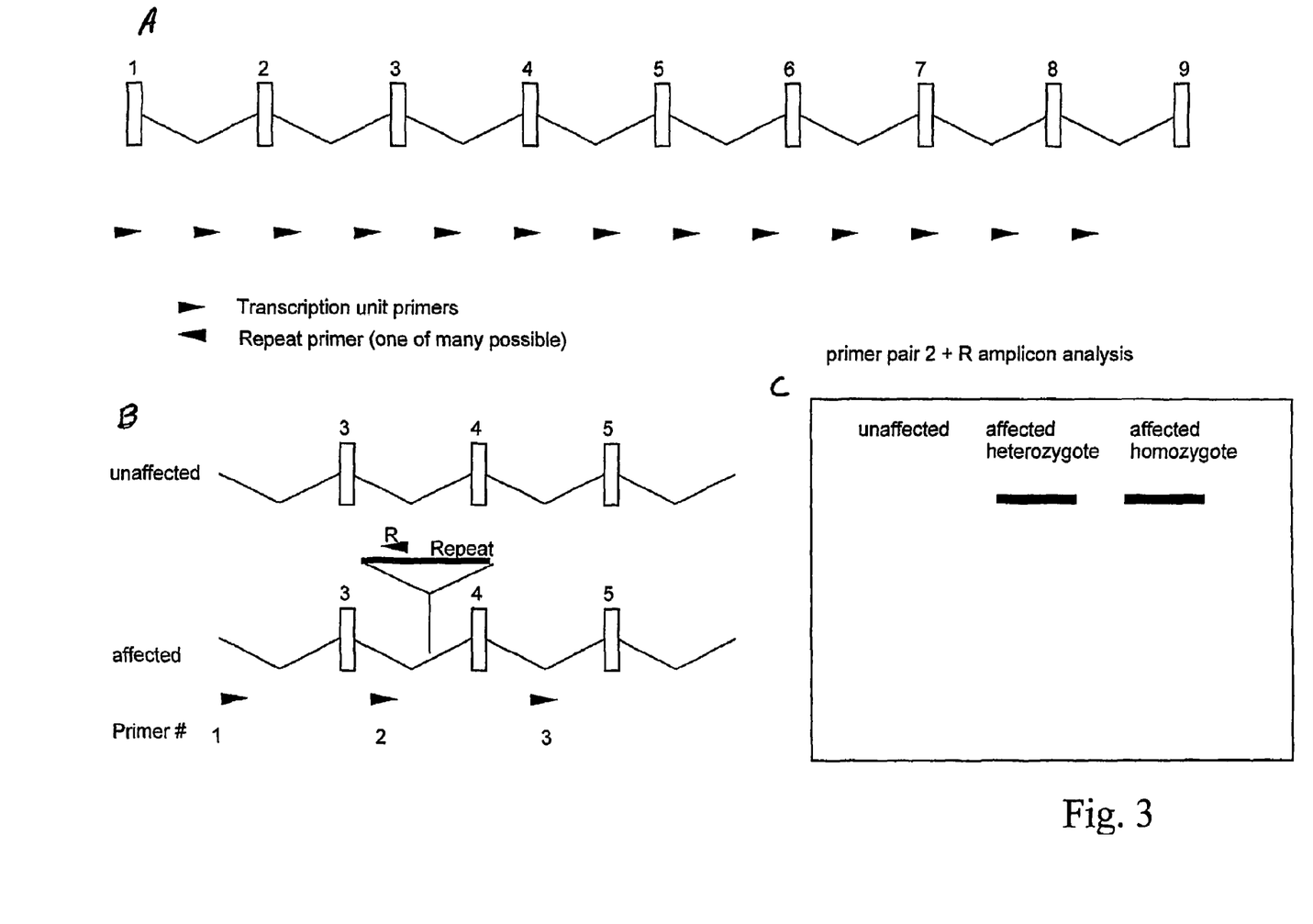
FIG. 3 shows a method for identifying repeat insertions based on comprehensive amplicon analysis using gene-specific primers in combination with repeat-specific primers.

This method is outlined in FIG. 3. Individual primers located throughout a transcription unit will be used in combination with a variety of retrotransposon or other repeat-specific primers to amplify certain portions of genomes from affected and unaffected indicuduals. If the gene-specific primers are labeled (fluorescently or radioactively, e.g.) the amplicons could once again be visualized on gels and new bands present in affecteds versus unaffected controls could be sought. At least two primer pairs (corresponding to the two possible orientations of the repeat relative to the target) may be required for each type of retrotransposons family screened.

Example 3

Human Repeat Array (HuRA) Detection Method.

Figure 4:
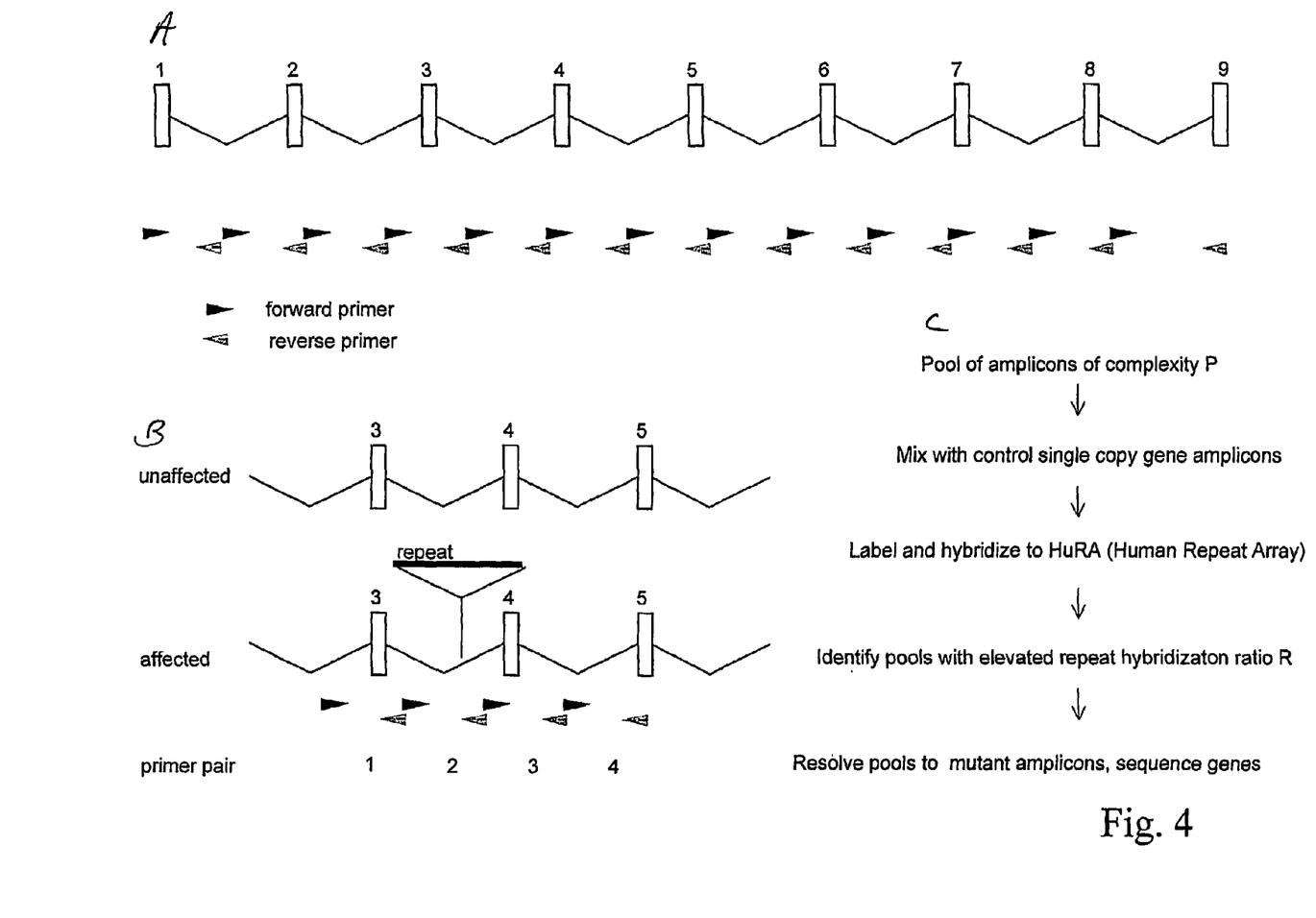
FIG. 4 shows the method for identifying repeat insertions based on comprehensive amplicon length analysis followed by hybridization to a Human Repeat Array (HuRA).

This method is outlined in FIG. 4. This method begins with the steps outlined in Method 2—PCR (polymerase chain reaction) or related DNA amplification methods are employed in the first step.

Primer pairs amplify insertion alleles up to 6 kb longer than the distance between the primer pairs. The primer pairs may are spaced every 1000 nucleotides throughout the transcription unit of interest and long PCR or a related amplification technique could be used to amplify the segments.

The amplicons are analyzed with the Human Repeat Array (FIG. 5), ideally containing all known human repeat sequences, which can be found in the publicly available human genome sequence. For example, the modern human L1 sequence, L1Hs, represented by a consensus sequence of about 6000 nucleotides, could be split into overlapping or nonoverlapping oligonucleotides of length "o". With the assumption that "o" is 60 nucleotides. Thus, the array component corresponding to L1Hs would consist of about 100 60-mers. Such arrays could be inexpensively fabricated by a wide variety of methods well-known in the art.

Figure 5:
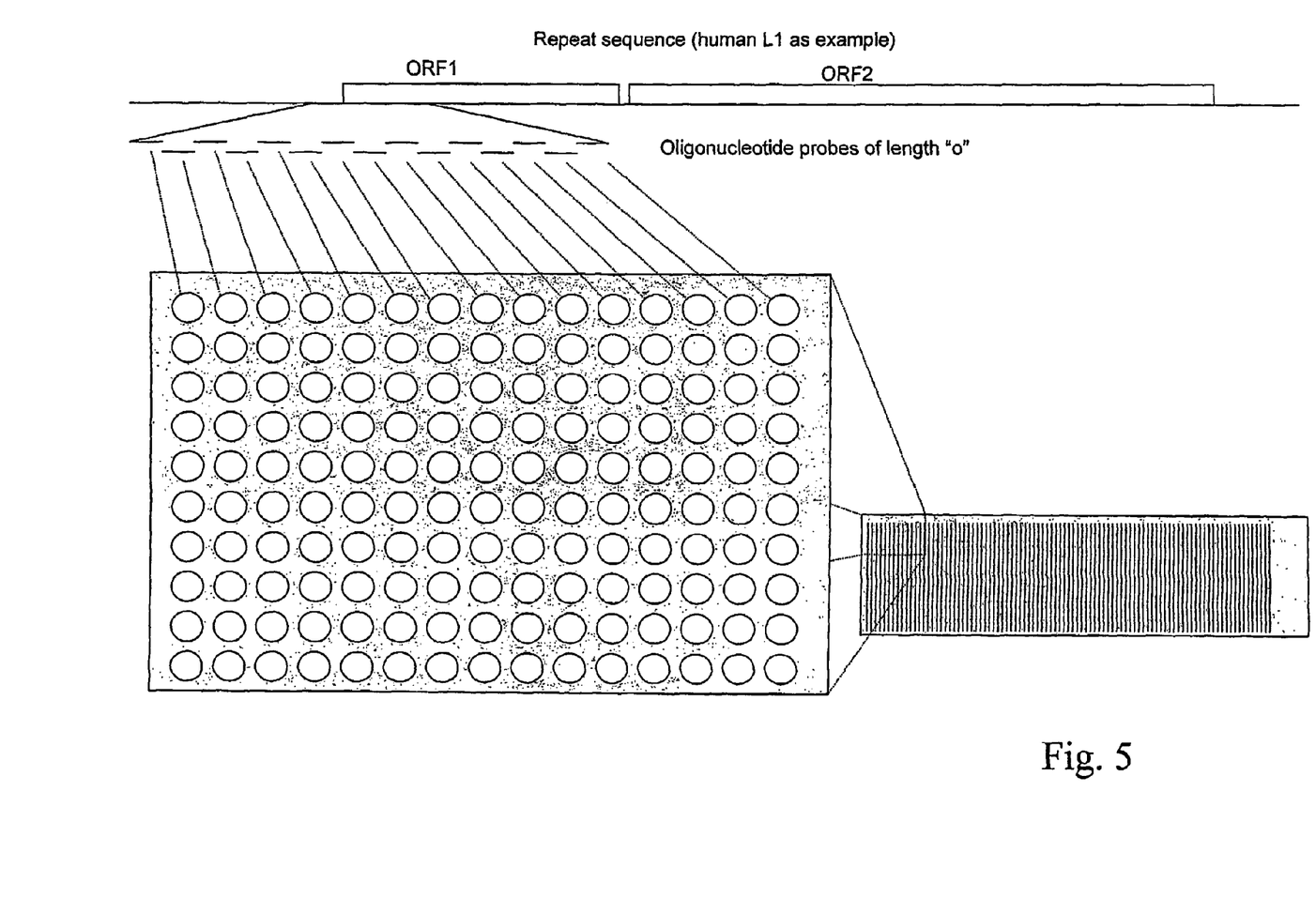

A preferred design would contain oligonucleotide sequences of length o (also referred to as "probes") spanning all known human repeat sequences. It would also contain probes spanning one or more single copy gene sequences for use as internal hybridization controls.

Amplicons from multiple reactions are pooled "P", labeled with a fluorescent molecule, and hybridized to the HuRA. The optimal value of P will have to be determined empirically. A control amplification product derived from one or more single copy genes would also be obtained from each affected individual. These could be admixed after amplification or the amplification reactions could be multiplexed as is well known in the art. If one or more amplicons contained human repeat sequences present in the affected samples and absent from the normal samples, the ratio "R" would increase. "R" is the average hybridization intensity of a probe derived from a repeat segment in an individual divided by the average hybridization intensity of the control single copy gene probe(s) from that same individual. This is also known as the repeat ratio "r". The repeat ratio for an affected individual is referred to as "ra" and for an unaffected individual (or pool of unaffected individuals) is referred to as "ru". R is thus defined as ra/ru. R is expected to be high for any probe corresponding to a repeat sequence present in the affected individual and absent from the unaffected individual(s). This method allows for statistical power because there would be dozens to hundreds of adjacent probes corresponding to each repeat, and R would be independently calculated for each of these probes. This allows for cost savings by increasing interprimer distance D and increasing amplicon pool size P. Other advantages include having all repeat sequences represented on the array as probes (tiling) is the ability to provide immediate information on the endpoints of the insertion because L1 and other repeat sequences are often truncated. Positive results can be stratified by insertion length—the longer the insertion, the higher the probability of a deleterious effect on gene expression.

This method may be automated. An example of the automation protocol is outlined in FIG. 6. For example, DNA sequence blocks are downloaded into a computer program; the blocks could correspond to genes or contiguous blocks of genomic sequence of any size. Known repeats in the sequence are masked to prevent a primer picker program to assign primers to repetitive regions. Primer picker programs are known in the art, for example, REPEATMASKER and the like are useful. A primer picker program chooses pairs of oligonucleotides spaced approximately D base pairs apart. The output from the primer picker program would serve as input to a high throughput oligonucleotide synthesizer. These are well-known in the art and could produce oligonulceotides in 96-well or 384 well format or any other high throughput format. The oligonucleotides, as well as the DNA templates would be combined using a liquid handler with reagents required for the amplification reaction, carried out in 96- or 384 well format or any other high throughput format. The amplification reaction, such as long PCR would then be performed. The liquid handler would then pool the amplicons in pools of size "P". Pooling is required to increase throughput and minimize costs, however, pooling is an optional step. The amplicons are labeled (this could occur during the synthesis of the oligonucleotides, and hybridized to HuRA arrays, which are scanned by a fluorescent or radioactive scanner.

Figure 6:
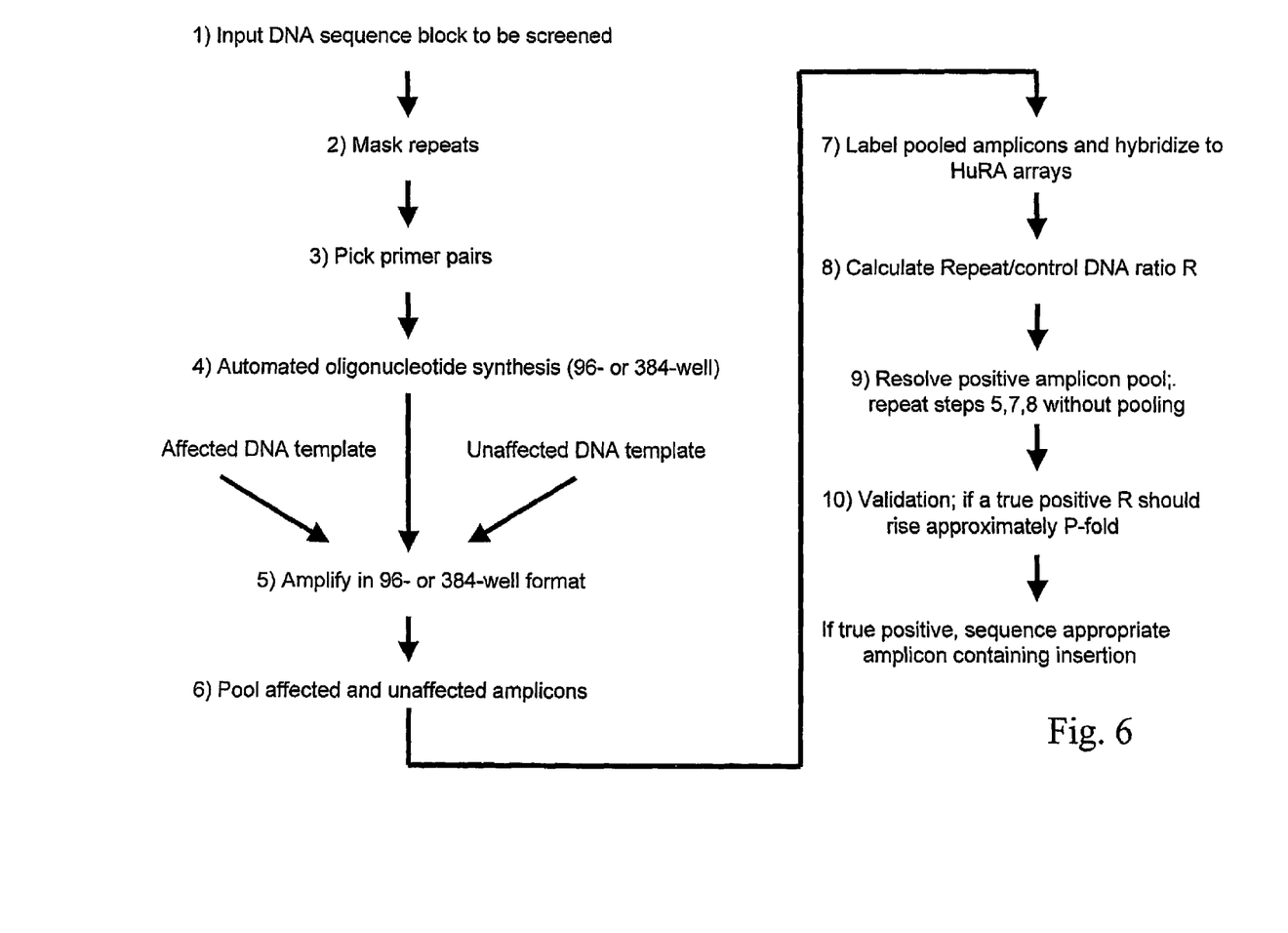
FIG. 6 shows a scheme for automating Method 4.

The repeat to control DNA ratio "R" is calculated as outlined above from the fluorescence or radioactivity values. If samples were pooled, the pools can be resolved by reamplifying the pools and continuing the protocol from that step. This may also serve as a validation step; if the positive amplicon identified is true, R should rise approximately P-fold in the appropriate unpooled sample. Finally, validate positives may be sequenced.

The HuRA would ideally represent all known human repeats, or a combination of human repeat sequences. For example, repeats identified by Lander (2001) and Smit (1996), as well as the 4 families of SINEs, 100 families of LTR-retrotransposons or endogenous retroviruses, the trinucleotide repeat expansion sequence families, approximately 60 families of DNA transposons and related sequences. DNA microarrays with hundreds of thousands of individual oligonucleotides are now in common use and thus all human repeat sequences can be represented on a single array. It is worth mentioning that many of the retro/DNA transposon families alluded to in these publications lack active members in *Homo sapiens*, indicating that their activities were likely extinguished in ancient evolutionary times. Nevertheless insertion alleles in our population could be ancient as in the case of Fukuyama muscular dystrophy (Kobayashi et a. 1998). Therefore a comprehensive array including ancient repeats will be more valuable than a non-comprehensive one. Finally, other repeated sequences that are not known to be transposable should be included, including rDNA, tRNAs, and satellite DNAs. It is conceivable that these may have some limited mobility or have had it in the past.

HuRA designs can be optimized by varying oligonucleotide length and systematically. Its performance on model targets can be evaluated to determine the optimal length. In principle, the oligonucleotides should be at least 20 nucleotides long to prevent cross hybridization. Longer oligonucleotides increases the increase specificity. Oligonucleotides longer than about 30 nucleotides is preferable to capture repeat variants that are present but that have one or a few mismatches to each oligonucleotide sequence. That is, such oligonucletides will probably increase the yield of useful repeat hybridization intensity.

The placement of the primer pairs (separated by distance "D" in FIG. 2) may be complicated by the presence of pre-existing repeat DNAs. If these are masked, there may be limited locations from which to choose a second primer exactly distance D away from the first primer. The second primer may be moving to the next available unique sequence either to the left or right of the pre-existing repeat.

Figure 7:
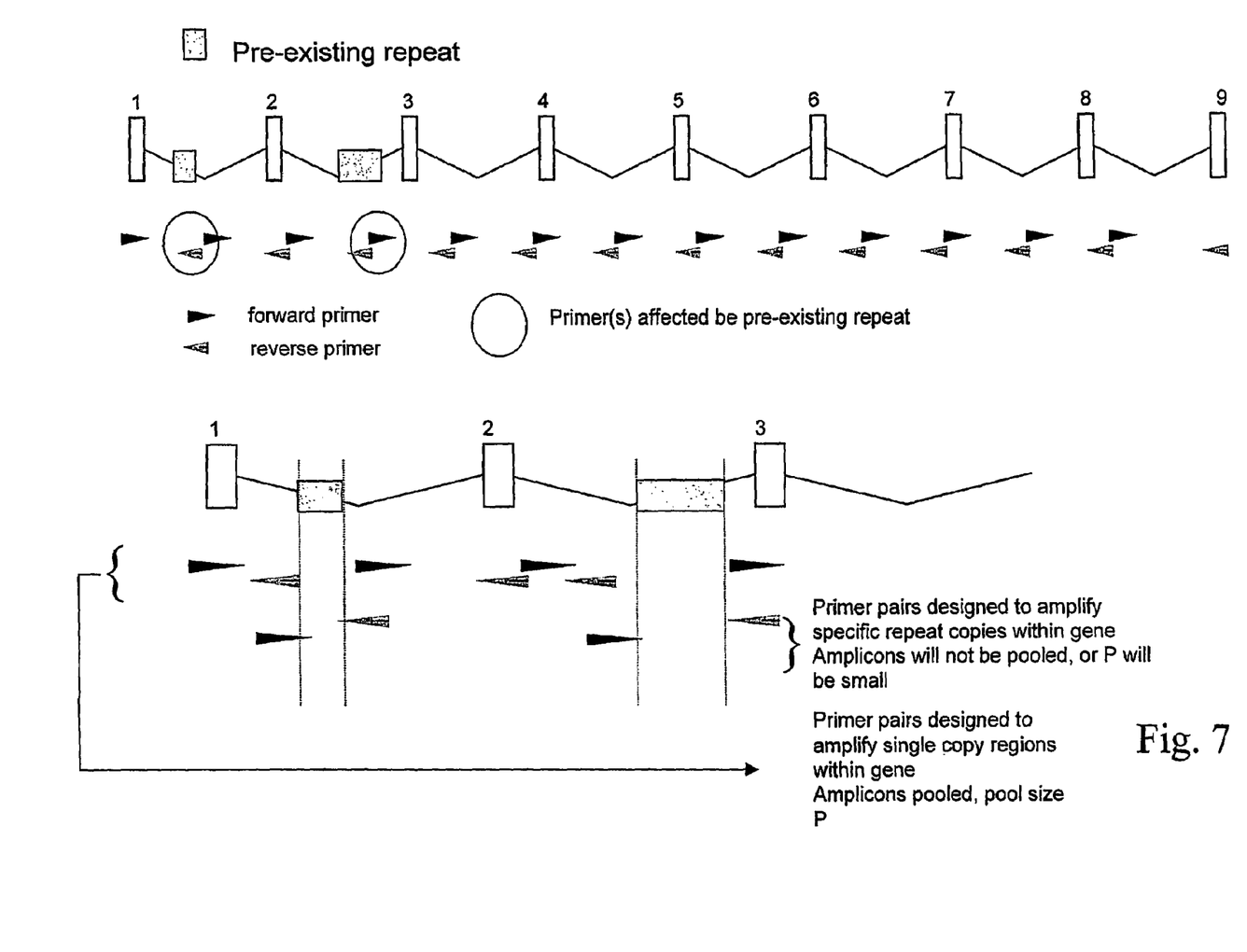
FIG. 7 demonstrates a method of minimizing the consequence of pre-existing repeat sequences in the gene to be analyzed.

Pre-existing repeat sequences in the transcription unit or gene being tested will provide "background noise" to the value of "r". That is, the ratio of repeat hybridization signal to control single gene hybridization signal will be finite. Thus the difference between ra and ru will be rather small, resulting in a value of "R" near 1. Thus the pre-existing repeat-specific signal will interfere with the ability to detect new insertions. To minimize this, it is possible to position the primers to directly flank pre-existing repeat sequences, rather than spacing them at a fixed distance from each other (for the purpose of calculating "D", the mean or median distance can still be used). For human DNAs for example, L1 and Alu sequences have the highest copy number, thus primers could be designed flank these sequences. This would result in the amplification of the nonrepetitive segments of genes, making the "unaffected" repeat hybridization signal for such amplicons very low (approaching zero) and therefore maximizing the value of R and allowing a higher value of P to be used. A complementary series of amplicons containing the pre-existing repeats could still be amplified, and these segments could be analyzed without pooling (or with a lower value of P) so that even modest values of R would still be detected. This variation on the first step of this method is summarized in FIG. 7.

This method may be easily adapted to cover intergenic regions. Insertions in integenic regions could have deleterious effects by providing a nidus of cytosine methylation or silence adjacent gene expression through other mechanisms. The gene-specific primers may be spaced throughout flanking regions upstream and downstream of the transcription unit(s) under study. Identical HuRA arrays could be used for detection as outlined above to detect these insertions.

This method has been shown with an example of a single gene. However may be expanded to include all genes, because every step is readily amenable to automation.

Example 4

Expansion of Scope—Classification of Cancers and Other Diseases

It is well known that cancer is a genetic disease characterized by extensive genome rearrangement. Moreover, there is evidence that certain types of tumors are associated with increased retrotransposition (Bratthauer and Fanning, 1992; Asch et al. 1996). The method of this invention could be applied to the classification of tumors and might be very useful for stratifying tumors into clinically predictive subtypes.

Example 5

Animal and Plant Health

The methods of the invention may be used to map complex traits in plants and animals, even with incomplete genome sequence information.

Example 6

Diagnostic Methods

The methods of the invention may be used to diagnosis subjects and individuals having diseases potentially caused by repeat insertion mutations. For example, the methods disclosed herein may be useful for diagnosing cancer, repeat expansion disorders, neurological disorders, and other diseases previously unknown to be caused by repeat insertion mutations.

While the invention has been disclosed with reference to specific embodiments, it is apparent that other embodiments and variations of the invention may be devised by others skilled in the art without departing from the true spirit and scope of the invention. The appended claims are intended to be construed to include all such embodiments and equivalent variations.

What is claimed is:

1. A method for identifying a repeat insertion mutation, comprising: i. hybridizing copies of one or more DNA segments from mammalian subjects affected and unaffected by the mutation to a Repeat Array; ii. detecting repeat insertions using gene specific primers in combination with repeat-specific primers; and iii. determining the ratio of segments containing human repeat sequences present in affected subject samples relative to repeat sequences present in unaffected subject samples, thereby identifying a repeat insertion mutation.

2. the method of claim 1, wherein the Repeat Array is a Human Repeat Array.

3. The method of claim 1, wherein the repeat insertion mutation is an L1 insertion mutation.

4. The method of claim 1, wherein DNA copies are generated by long polymerase chain reaction using primer pairs.

5. The method of claim 4, wherein primer pairs are spaced about 1000 nucleotides or less apart.

6. The method of claim 1, wherein the primer pairs are spaced more than about 1000 nucleotides apart.

7. The method of claim 2, wherein the Human Repeat Array contains all known human repeat sequences.

8. The method of claim 2, wherein the Human Repeat Array contains oligonucleotide probes of a length spanning all known human repeat sequences.

9. The method of claim 2, wherein the Human Repeat Array includes both repeat sequences known to be transposable and repeat sequences not known to be transposable.

10. The method of claim 9, wherein the repeat sequences not known to be transposable include rDNAs, tRNAs, satellite DNAs, and expandable DNAs.

11. The method of claim 8, wherein each oligonucleotide probe is at least about 30 nucleotides in length.

12. The method of claim 8, wherein each oligonucleotide probe is less than about 200 nucleotides in length.

13. The method of claim 12, wherein each oligonucleotide probe is less than about 100 nucleotides in length.

14. The method of ciaim 1, wherein said method is not limited to a single DNA segment of interest.

15. A method for identifying or classifying genetic diseases characterized by genome rearrangement, comprising: i. hybridizing copies of one or more DNA segments from mammalian subjects affected and unaffected by the genetic disease to a Repeat Army; ii. detecting repeat sequences using gene specific primers in combination with repeat-specific primers; and iii. determining the ratio of segments containing human repeat sequences present in affected subject samples relative to repeat sequences present in unaffected subject samples.

16. The method of claim 15, wherein the repeat array is a human repeat array.

17. The method of claim 15, wherein the identification or classification is directed to types of tumors.

18. A method for mapping complex traits controlled by repeat insertion mutations in a plant or mammalian subject, comprising: i. hybridizing copies of one or more DNA segments from said subject exhibiting and not exhibiting the trait to a Repeat Array; ii. detecting repeat sequences using gene specific primers in combination with repeat-specific primers; and iii. determining the ratio of segments containing repeat sequences present in trait-exhibiting subject samples relative to repeat sequences present in non-trait-exhibiting subject samples.

19. A method for diagnosing complex traits in a plant or mammalian subject, comprising: i. hybridizing copies of one or more DNA segments from said subject exhibiting and not exhibiting the trait to a Repeat Array; ii. detecting repeat sequences using gene specific primers in combination with repeat-specific primers; and iii. determining the ratio of segments containing repeat sequences present in trait-exhibiting subject samples relative to repeat sequences present in non-trait-exhibiting subject samples.

* * * * *